(12) United States Patent
Pappas

(10) Patent No.: US 6,764,516 B2
(45) Date of Patent: *Jul. 20, 2004

(54) POSTERIOR STABILIZED KNEE REPLACEMENT WITH BEARING TRANSLATION FOR KNEES WITH RETAINED COLLATERAL LIGAMENTS

(75) Inventor: Michael J. Pappas, Caldwell, NJ (US)

(73) Assignee: Biomedical Engineering Trust I, South Orange, NJ (US)

(*) Notice: Subject to any disclaimer, the term of this patent is extended or adjusted under 35 U.S.C. 154(b) by 74 days.

This patent is subject to a terminal disclaimer.

(21) Appl. No.: 10/165,381

(22) Filed: Jun. 7, 2002

(65) Prior Publication Data

US 2002/0156535 A1 Oct. 24, 2002

Related U.S. Application Data

(63) Continuation of application No. 09/796,281, filed on Feb. 28, 200.1
(60) Provisional application No. 60/188,714, filed on Mar. 13, 2000.

(51) Int. Cl.⁷ .................................................. A61F 2/38
(52) U.S. Cl. .......................... 623/20.29; 623/20.27; 623/20.21; 623/20.15
(58) Field of Search .......................... 623/20.29, 20.27, 623/20.21, 20.28, 20.33, 20.34, 20.15, 20.19, 20.14

(56) References Cited

U.S. PATENT DOCUMENTS

| | | | |
|---|---|---|---|
| 4,213,209 A | * | 7/1980 | Insall et al. .............. 623/20.27 |
| 4,249,270 A | * | 2/1981 | Bahler et al. ............ 623/20.27 |
| 4,298,992 A | * | 11/1981 | Burstein et al. ......... 623/20.27 |
| 4,309,778 A | | 1/1982 | Buechel et al. |
| 4,470,158 A | | 9/1984 | Pappas et al. |
| 4,568,348 A | | 2/1986 | Johnson et al. |
| 4,634,444 A | | 1/1987 | Noiles |
| 4,888,021 A | | 12/1989 | Forte et al. |
| 4,950,298 A | * | 8/1990 | Gustilo et al. ........... 623/20.15 |
| 5,330,534 A | | 7/1994 | Herrington et al. |
| 5,395,401 A | * | 3/1995 | Bahler ..................... 623/20.29 |
| 5,489,311 A | | 2/1996 | Cipolletti |
| 5,658,342 A | | 8/1997 | Draganich et al. |
| 5,824,100 A | * | 10/1998 | Kester et al. ............ 623/20.31 |
| 6,099,570 A | * | 8/2000 | Livet et al. .............. 623/20.21 |
| 6,117,175 A | * | 9/2000 | Bosredon ................ 623/20.15 |
| 6,206,926 B1 | * | 3/2001 | Pappas .................... 623/20.27 |
| 6,475,241 B2 | * | 11/2002 | Pappas .................... 623/20.29 |
| 6,491,726 B2 | * | 12/2002 | Pappas .................... 623/20.29 |

* cited by examiner

*Primary Examiner*—Pedro Philogene
(74) *Attorney, Agent, or Firm*—Anthony J. Casella; Gerald E. Hespos

(57) ABSTRACT

A knee joint prosthesis includes femoral and tibial components, a bearing and a control arm. The bearing includes an inferior surface in sliding bearing engagement with the tibial component and a superior surface in articular bearing engagement with the femoral component. A notch extends into the posterior end of the bearing and a groove extends anteriorly from the notch in the inferior surface of the bearing. The posterior portions of the femoral component define a cam box having medial and lateral walls and a cam extending therebetween. The control arm is slidably engaged in the groove of the bearing and pivotally engage on the tibial component. The control arm further includes a post that extends into the cam box. The post includes a cam surface that engages the femoral cam to generate roll back of the femoral component on the bearing during flexion. Roll back substantially avoids climb of the femoral component on the bearing during flexion and hence reduces shearing forces on the post.

15 Claims, 9 Drawing Sheets

FULL EXTENSION

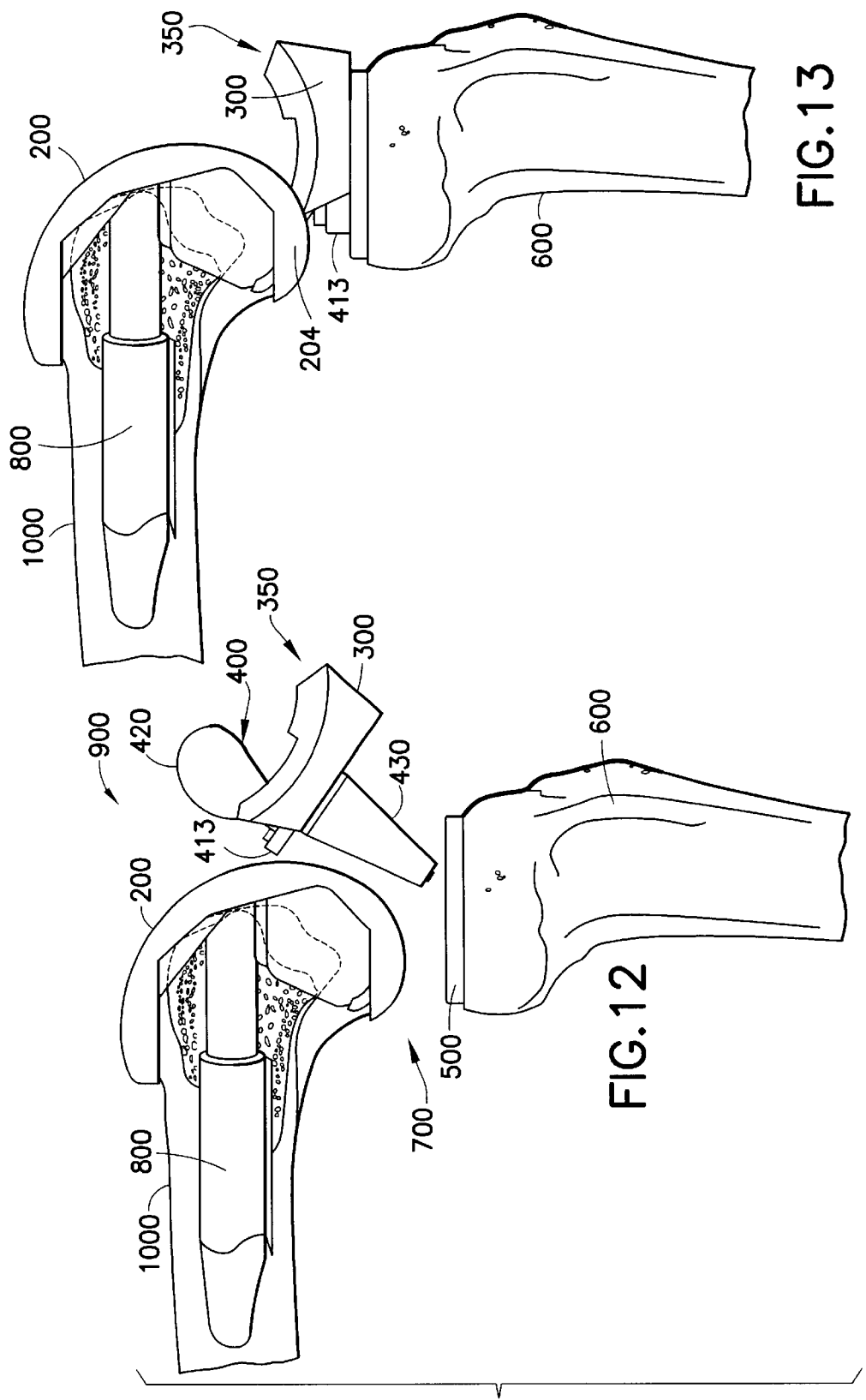

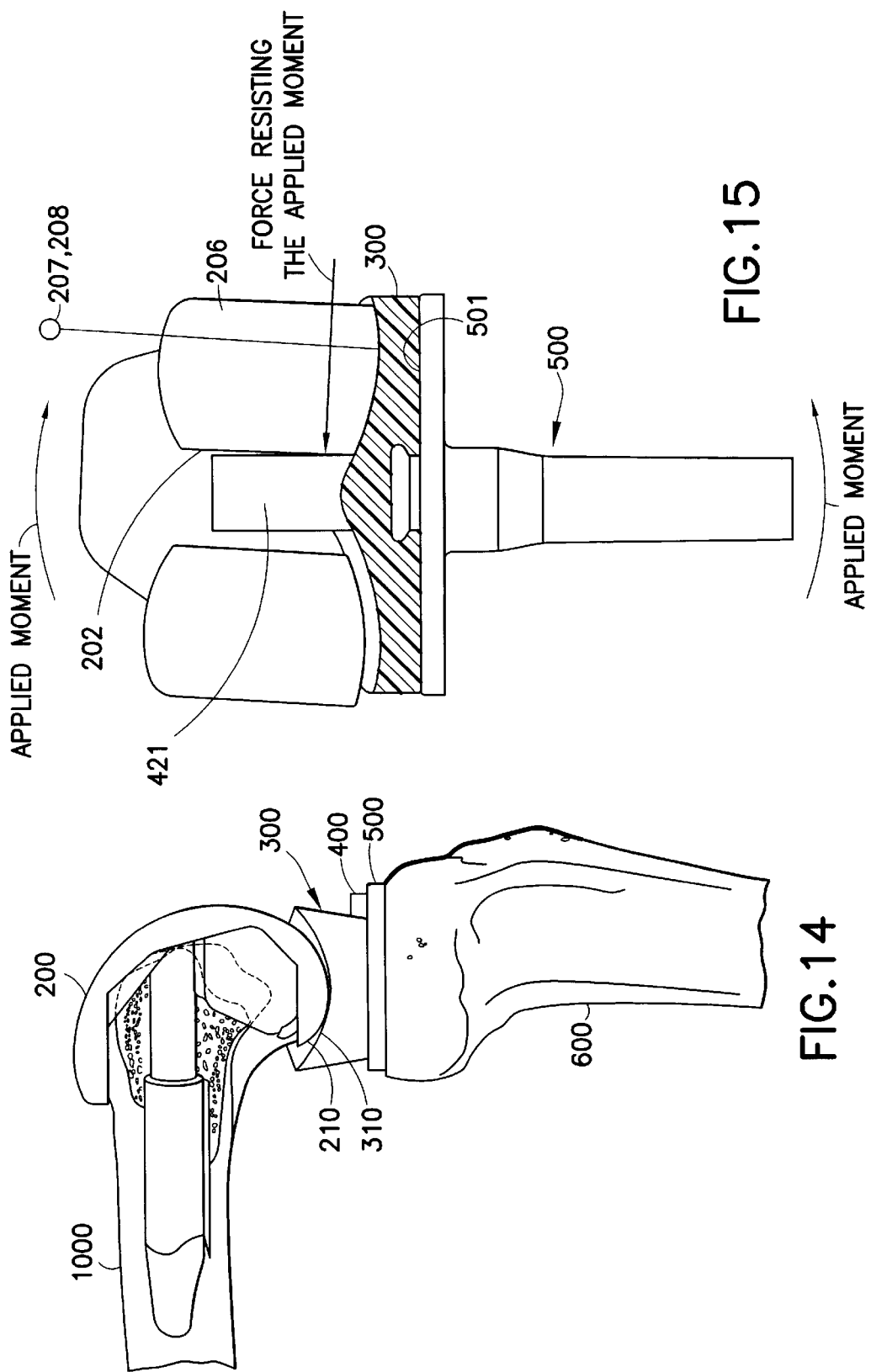

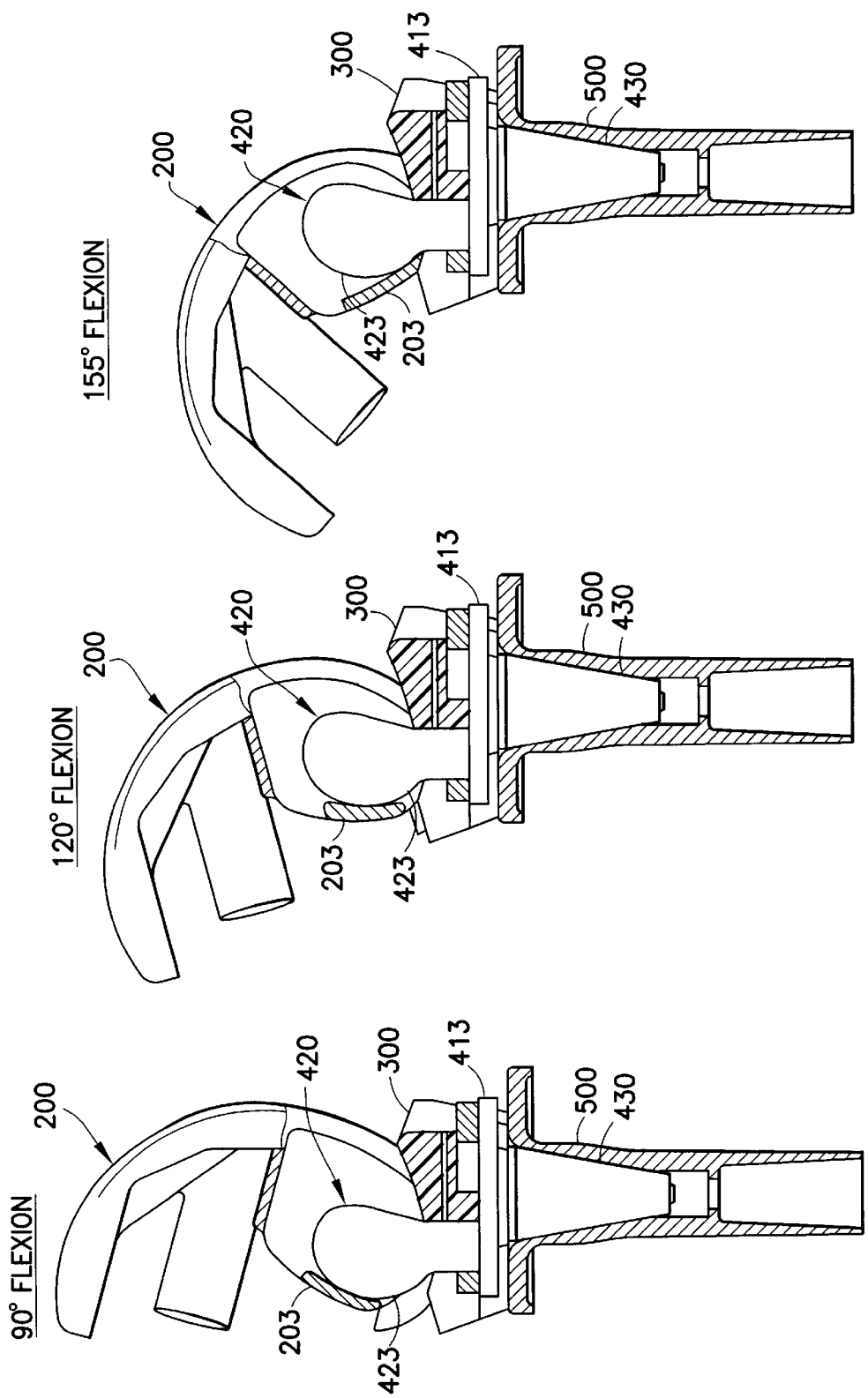

POSTERIOR STABILIZED KNEE REPLACEMENT WITH BEARING TRANSLATION FOR KNEES WITH RETAINED COLLATERAL LIGAMENTS

This application is a continuation of U.S. patent application Ser. No. 09/796,281, filed Feb. 28, 2001. This application claims benefit of Provisional Application No. 60/188,714 filed Mar. 13, 2000.

BACKGROUND OF THE INVENTION

1. Field of the Invention

The subject invention relates to a knee joint prosthesis, and particularly a posterior stabilized replacement knee joint prosthesis.

2. Description of the Related Art

A natural knee joint includes the distal end of the femur with articular cartilage, the proximal end of the tibia with articular cartilage and a meniscus between the femur and tibia. The femur and the tibia are held in a proper relationship to the bearing by ligaments. These stabilizing ligaments include the posterior cruciate ligament, the anterior cruciate ligament and collateral ligaments.

Flexion of the knee causes the tibia to rotate relative to the femur about an axis that extends generally in a medial-to-lateral direction and simultaneously causes the contact area of the femur to roll back relative to the tibia. Flexion also generates rotation of the tibia about its own axis. The amount of rotation of the tibia during flexion of the knee is controlled and limited by the ligaments.

The natural knee joint can become damaged or diseased. For example, damage or disease to the knee can deteriorate the articular surfaces of the femur or tibia and can damage the articular cartilage between the bones. The prior art includes prosthetic knee joints to replace a damaged or diseased natural knee. A prosthetic knee joint typically includes a femoral component that is mounted to the distal end of a resected femur, a tibial component mounted to the proximal end of a resected tibia and a bearing between the femoral and tibial components. The inferior face of the femoral component of a prosthetic knee joint typically defines a pair of arcuate convex condyles. The superior face of the bearing has a corresponding pair of arcuately concave regions for articular bearing engagement with the condyles of the femoral component. The superior face of the tibial component may be substantially planar and is disposed in engagement with the inferior face of the bearing.

Prior art prosthetic knee joints have taken many different forms, depending upon the preferences of the orthopedic surgeon, the condition of the natural knee and the health, age and mobility of the patient. Some prior art knee joint prostheses fixedly secure the inferior surface of the bearing to the superior surface of the tibial component. Other prior art knee joint prostheses permit rotational movement between the bearing and the tibial component. Still other prior art knee joint prosthesis permit a controlled amount of anterior-posterior sliding movement between the bearing and a tibial component. Movement of the bearing relative to the tibial component achieves many functional advantages, as described in the prior art. Prior art knee joint prostheses that incorporate certain of the structural and functional features referred to above are disclosed in U.S. Pat. Nos. 4,470,158 and 4,309,778.

As noted above, the inferior bearing surface of the femoral component on most prosthetic knee joints comprises a pair of convexly arcuately condyles. The condyles of the femoral component are in articular bearing engagement with arcuately concave regions on the superior face of the bearing. Thus, the superior face of the bearing typically includes a pair of dished regions each of which has a relatively depressed center portion and a relatively elevated peripheral lip. As explained above, flexion of the knee joint causes the tibia to rotate about a medial-lateral axis relative to the femur. Flexion also causes the tibia to rotate around its own axis. These combined movements cause the condyles of the femur to ride up or climb the concavities on the superior surface of the bearing and to approach the peripheral lips of the bearing. Thus, flexion tends to move the relative components of the prosthetic knee toward dislocation. The degree to which dislocation is possible depends on several factors, most significantly, the presence or absence of ligaments. The likelihood of dislocation also depends upon the degree of flexion and on the degree of congruency between the inferior articular bearing surface of the femoral component and the superior surface of the bearing. For example, climbing of the femoral component on the bearing is not a significant problem in prosthetic knees that have a substantially flat superior surface on the bearing. However, the relatively great incongruency between the inferior bearing surface of the femoral component and the superior surface of the bearing on these prosthetic knees results in a very high contact stress that can damage the bearing. Prosthetic knees that have greater congruency between the femoral component and the bearing provide desirably low contact stress. However, the greater congruency when combined with a bearing that is slidable on the tibial component creates the problem of the tibial component climbing on the bearing, and hence creates the potential of dislocation. Climbing of the femoral component on the bearing also is a particular problem for prosthetic knee joints that employ a posterior stabilization post. In particular, the climbing of the femoral component on the bearing substantially increases sheer forces on the post and can lead to traumatic failure of the prosthesis.

Valgus-varus stability of a knee joint refers to the ability of the joint to resist the lateral forces or rotary forces that would cause rotation of the tibia relative to the femur in the frontal plane. Lateral forces or rotary movements that cause rotation of the tibia relative to the femur in the frontal plane tend to create a dislocation. Such dislocation is particularly likely to occur on either the medial or lateral side of the prosthesis, depending upon the direction of the lateral forces. Such a dislocation in a prior art prosthesis is shown in FIG. 18 hereto.

The prosthetic knee joint is under a compressive loading during normal activities. As a result, valgus-varus moments typically are resisted adequately by the articulating surfaces of the prosthetic components and by the ligaments. However, there are instances where additional valgus-varus stability may be desired, such as those instances where ligaments are deficient.

Some prior art prosthetic knee joints enhance valgus-varus stability by providing a stabilization post that extends into a posterior region between the femoral condyles. This region would be occupied by the posterior cruciate ligament if that ligament were present. Prosthetic knee joints that permit anterior-posterior sliding movement of the bearing on the tibial component provide superior roll back. In this regard, the term "roll back" refers to a posterior movement of the contact point of the femur relative to the tibia during flexion. Roll back, however, causes the femoral component to climb on the bearing, and thus increases the probability of dislocation. Additionally, this greater roll back and increases of climbing of the femoral component on the bearing substantially reduce shear forces on the posterior stabilizing post for those prosthetic joints that have such a posterior stabilizing post. A prosthetic bearing that can slide posteriorly during flexion avoids impingement between the bearing and anterior soft tissue of the knee. Thus, a prosthetic knee joint with a bearing capable of anterior-posterior sliding movement can avoid discomfort during deep flexion.

A prior art prosthetic knee joint with a stabilizing post and a bearing capable of anterior-posterior sliding movement is shown in U.S. Pat. No. 5,395,401 which issued to Bahler. In particular, U.S. Pat. No. 5,395,401 shows a prosthetic knee having a tibial component and a bearing slidably disposed on the superior face of the tibial component. The inferior surface of the bearing is provided with a dovetailed groove that extends along an anterior-posterior direction and at a location between the two concave condyles formed on the superior surface of the bearing. The bearing shown in U.S. Pat. No. 5,395,401 also includes a notch extending into the posterior portion of the bearing at a location between the two concave condyles of the bearing. The notch registers with the dovetailed groove of the bearing. The prosthesis of U.S. Pat. No. 5,395,401 further includes a control arm with a post that is pivotally engaged in a recess formed on the tibial component. The control arm includes a dovetailed portion that slidably engages in the dovetailed groove on the inferior surface of the bearing. The control arm shown in U.S. Pat. No. 5,395,401 also has a post that extends through the notch in the bearing and between the condyles of the femoral component. The post is dimensioned to slidably engage surfaces of the femoral component between the two convex condyles of the femoral component. However, nothing in U.S. Pat. No. 5,395,401 would prevent dislocation of the femur from the bearing.

The prior art includes other prosthetic components that have posterior stabilizing posts that extend unitarily from the bearing and into the space between the femoral condyles. Prior art prosthetic joints of this type are shown, for example, in U.S. Pat. Nos. 5,658,342; 5,489,311; 5,330,534; 4,950,298; 4,888,021; 4,634,444 and 4,568,348. All of these prior art prostheses are used for joint replacements where the posterior cruciate ligament cannot be retained or is deficient. Additionally, most of these prior art prosthetic components are for use when both collateral ligaments can be retained.

Despite the various attributes of the prior art prosthetic components, it is desired to provide a prosthetic knee joint that provides superior dislocation resistance than other non-hinged prosthetic knee joints.

It is another object of the subject invention to provide a prosthetic knee joint that avoids any significantly likelihood of dislocation while simultaneously permitting anterior-posterior sliding movement of the bearing relative to the tibial component.

It is a further object of the subject invention to provide a prosthetic knee joint with enhanced dislocation resistance and superior roll back.

Still another object of the subject invention is to provide a prosthetic knee joint that provides enhanced dislocation resistance and reduced sheer on a posterior stabilization post.

SUMMARY OF THE INVENTION

The subject invention is directed to a knee joint prosthesis with an ability to resist dislocation at high degrees of flexion, but without dislocation resistance at low flexion. The knee joint prosthesis of the subject invention also provides resistance to valgus-varus moments.

The prosthesis of the subject invention includes a tibial component, a femoral component, a bearing and a control arm assembly. The tibial component includes an inferior projection configured for secure mounting in a recess formed in a resected tibia. The tibial component further includes a superior bearing surface having a conical recess extending therein and disposed within portions of the tibial component that define inferior mounting projection.

The femoral component includes a superior surface with a projection for mounting in a recess formed in a resected distal end of a femur. The femoral component further includes an inferior surface defining a pair of convex articular condyles. A notch extends into the posterior end of the femoral component and defines a cam box. The cam box has a pair of substantially parallel spaced apart medial and lateral sidewalls and a femoral cam that extends between superior locations on the sidewalls of the cam box.

The bearing includes a superior surface having a pair of concave arcuate bearing surfaces in articular bearing engagement with the condyles of the femoral component. The bearing further includes an inferior surface disposed in sliding bearing engagement with the superior surface of the tibial component. A dovetail groove is formed in the inferior surface of the bearing, and extends generally in an anterior-posterior direction. The bearing further include a notch extending into the posterior side of the bearing and continuously between the superior and inferior surfaces thereof. The notch is substantially centrally disposed between the medial and lateral extremes of the bearing and registers with the dovetail groove. The anterior end of the notch may include an undercut or step that faces posteriorly and inferiorly. The undercut may engage a portion of the control arm at high degrees of flexion of the joint for resisting dislocation. However, at lower degrees of flexion, the undercut will play substantially no role in the normal operation of the joint. The inferior surface of the bearing may further include a stop recess near anterior portions of the dovetail groove. The stop recess may engage a stop pin on the control arm assembly to limit anterior movement of the bearing.

The control arm assembly includes a conical bearing dimensioned to pivotally engage in the conical recess formed in the tibial component. A dovetail guide extends substantially orthogonally from the superior large diameter end of the conical bearing of the control arm assembly. The dovetail guide is engageable in the dovetail groove formed in the inferior face of the bearing. The control arm further includes a post projecting in a superior direction from the posterior end of the control arm. The post is dimensioned to be received slidably in the notches in the posterior faces of the bearing and the femoral component. Portions of the post adjacent the control arm may define a control arm boss. The boss, if present, is configured to slide into the undercut at the anterior end of the notch in the bearing as the joint approaches maximum deflection. A stop pin may project in a superior direction from the anterior end of the dovetail guide for engagement in the stop recess of the bearing.

The prosthetic joint of the subject invention provides valgus-varus stability in two ways. Under loading conditions the normal compressive load will press the femoral condyles against the matching superior bearing surface of the bearing. The match is such that under compression any rotation of the femoral component occurs around an axis extending in an anterior-posterior direction. Rotation about such an axis produces impingement between the side surfaces of the post of the control arm and the sidewalls of the cam box. This contact produces a reaction force that resists any valgus-varus moment applied to the joint. During non-load bearing phases, where any valgus-varus moment is small, the post may be subject to small bending loads since joint compression will not exist under these conditions. However, the post can be made strong enough to resist such bending moments.

As flexion of the joint progresses, the box cam surface will engage the cam surface of the post. This engagement will commence at about 45° flexion. Flexion beyond about 45° will force the femoral component posteriorly. Compressive force on the bearing and its concave shape will cause the bearing to move with the femoral component. This posterior movement, or femoral rollback, improves quadricep effectiveness. Slightly beyond about 120° of flexion, it is desirable to prevent any additional posterior motion of the bearing. This can be accomplished by engagement between the post stop surface of the control arm and the recess stop surface defined by the undercut in the notch of the bearing.

BRIEF DESCRIPTION OF THE DRAWINGS

FIG. 12 is an exploded side elevational view showing implementation of the bearing.

FIG. 13 is a side elevational view similar to FIG. 12, but showing a later stage of implementation.

FIG. 14 is a side elevational view similar to FIGS. 12 and 13, but showing complete implementation.

FIG. 15 is a rear elevational view of the assembled prosthetic component schematically showing forces applied thereto.

FIG. 19 is a cross-sectional view similar to FIGS. 16–18, but showing approximately 90° flexion.

FIG. 20 is a cross-sectional view similar to FIGS. 16–19, but showing approximately 120° flexion.

FIG. 21 is a cross-sectional view similar to FIGS. 16–20, but showing approximately 155°.

DETAILED DESCRIPTION OF THE PREFERRED EMBODIMENT

Figure 1:
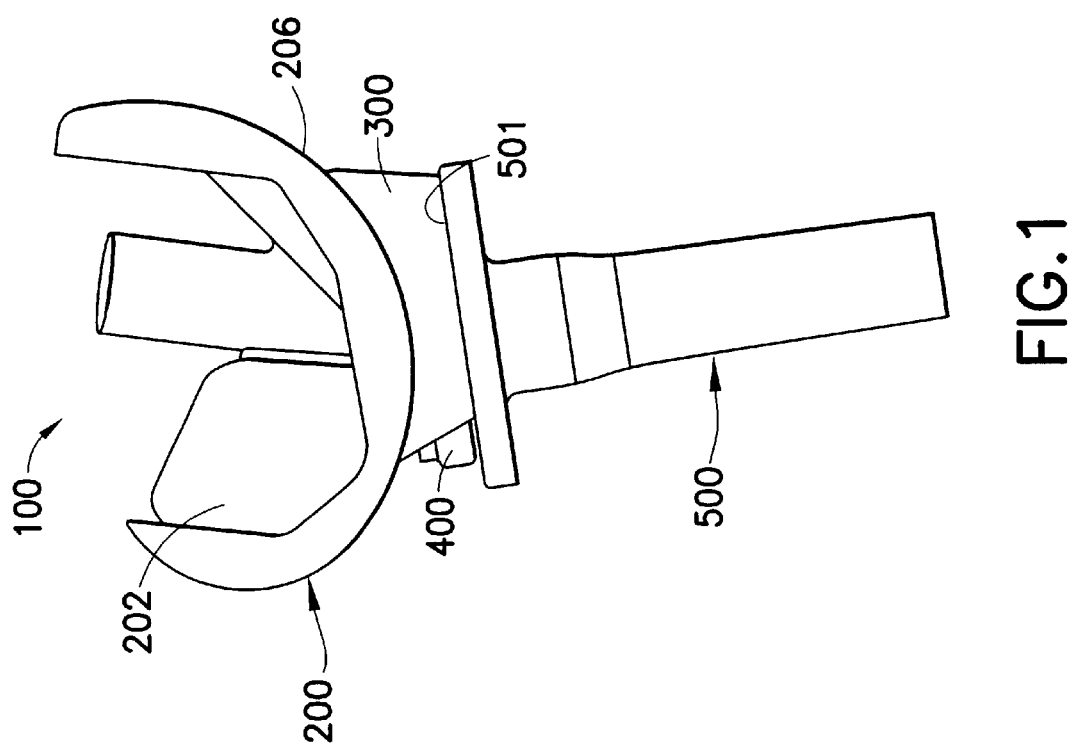
FIG. 1 is a side elevational view of a prosthetic joint in accordance with the subject invention.

The posterior stabilized knee replacement 100 consists of a femoral component 200, a bearing 300, a control arm assembly 400 and a tibial platform 500 as shown in FIG. 1.

Figure 2:
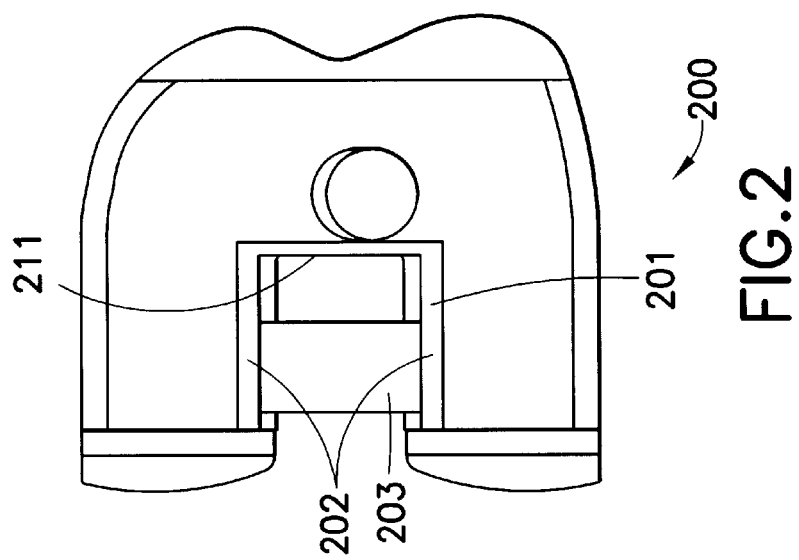
FIG. 2 is a top plan view of the femoral component of the prosthetic joint.
Figure 3:
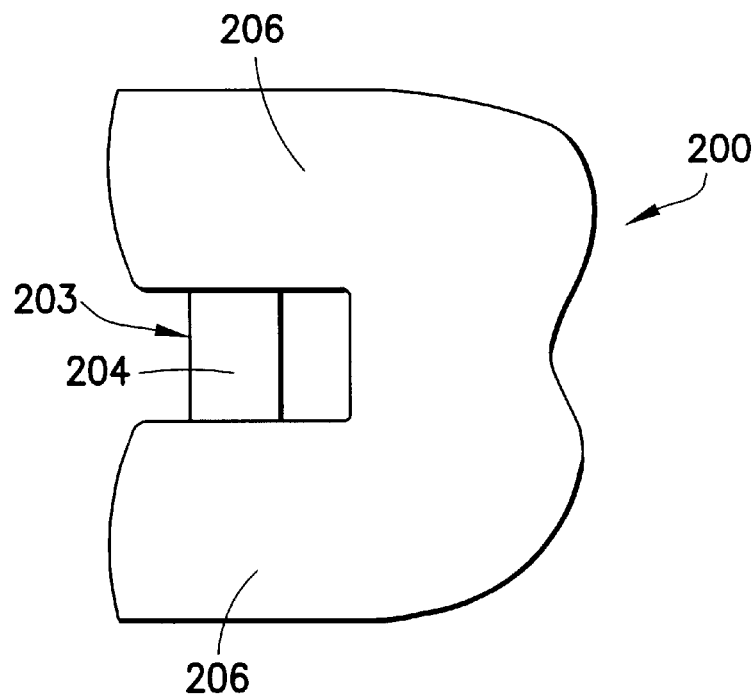
FIG. 3 is a bottom plan view of the femoral component.
Figure 16:
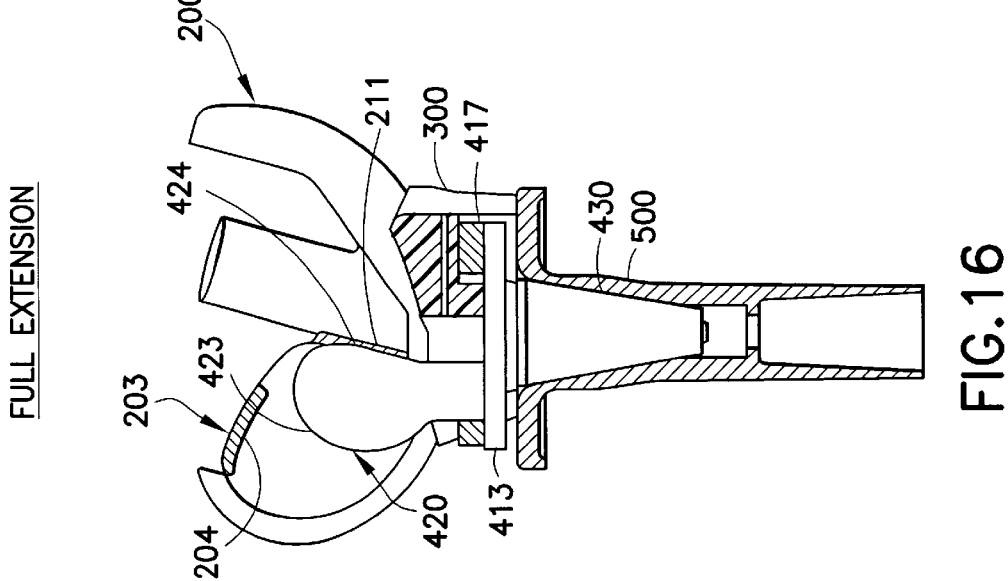
FIG. 16 is a cross-sectional view of the prosthetic joint at full extension.
Figure 22:
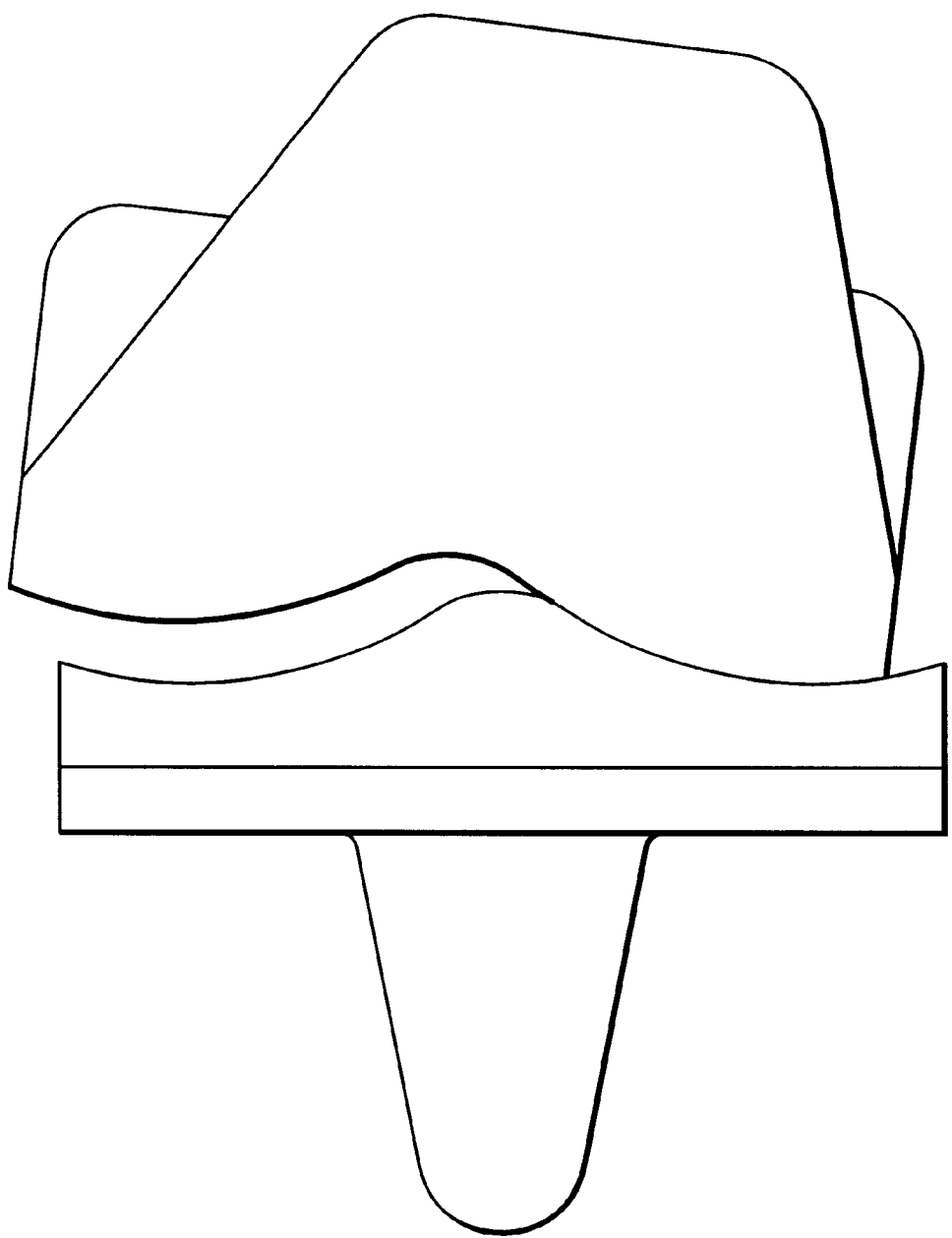
FIG. 22 is a rear elevational view of a prior art prosthesis showing dislocation.

The femoral component 200, as shown in FIGS. 2 and 3, contains a cam box 201 with box sidewalls 202 and femoral cam 203. The femoral cam 203 includes a cam surface 204 that faces inferiorly at full extension, as shown in FIG. 16. In the embodiment of FIGS. 1–19, the femoral cam surface 204 is a single concave surface. In other embodiments, the cam surface could be a compound curve with convex surfaces separated by a concave surface. The cam box 201 also includes an anterior wall 211. The femoral component 200 is similar to that described in U.S. Pat. No. 5,702,466 except for the addition of the cam box 201 detail and a modular post for accepting an extensions to provide enhanced fixation. More particularly, the femoral component 200 includes a pair of convex condyles 206 that face inferiorly for articular bearing engagement with the bearing 300, as explained below.

Figure 4:
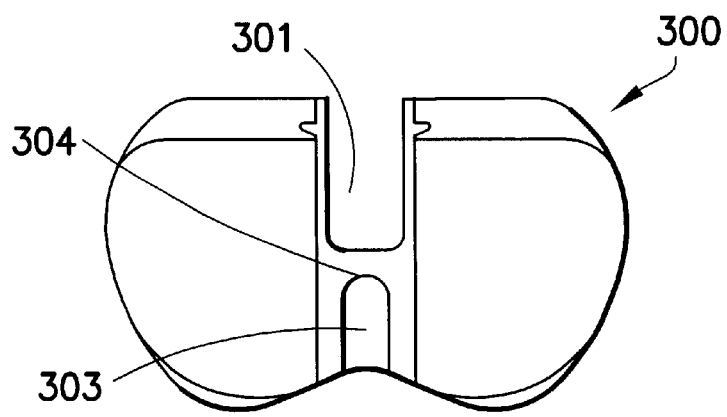
FIG. 4 is a bottom plan view of the bearing.
Figure 5:
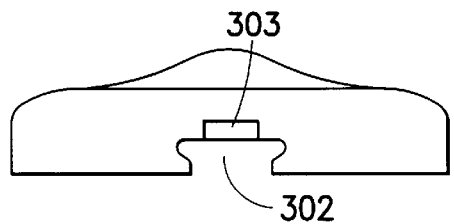
FIG. 5 is a front elevational view of the bearing.
Figure 6:
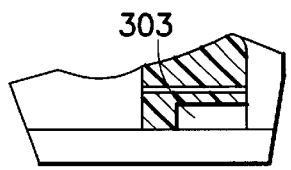
FIG. 6 is a cross-sectional view of the bearing.

The bearing 300, as shown in FIGS. 4–6, contains a posterior notch 301, a dovetail guide slot 302 and a stop recess 303 with a bearing stop surface 304.

Figure 7:
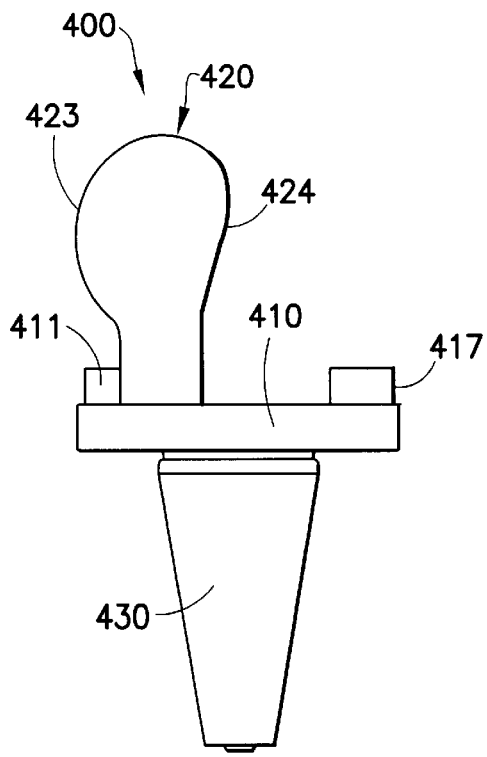
FIG. 7 is a side elevational view of the control arm.
Figure 8:
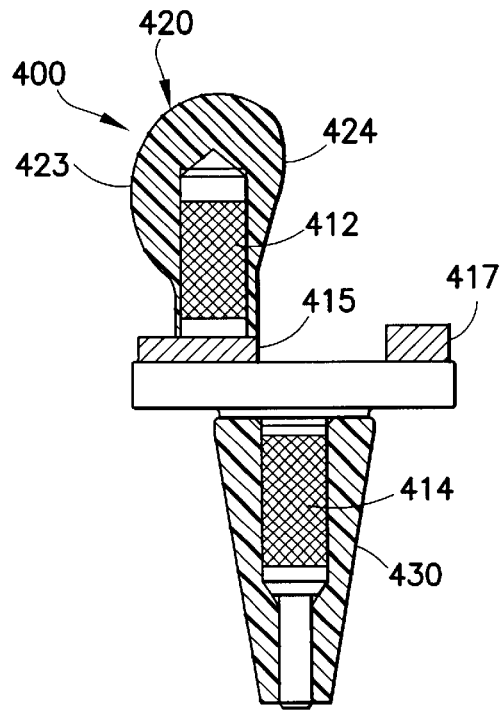
FIG. 8 is a cross-sectional view of the control arm.
Figure 9:
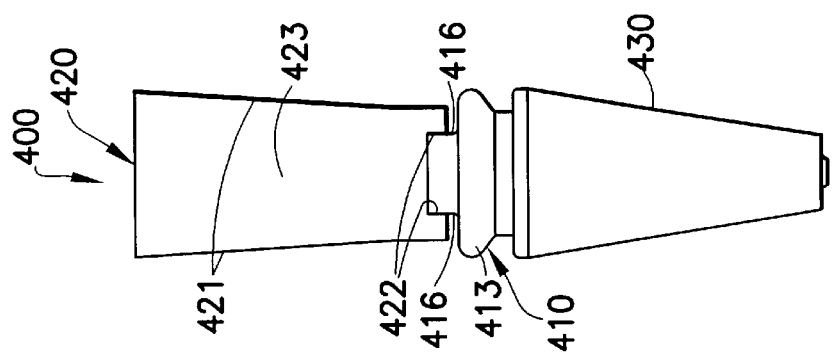
FIG. 9 is a rear elevational view of the control arm.
Figure 18:
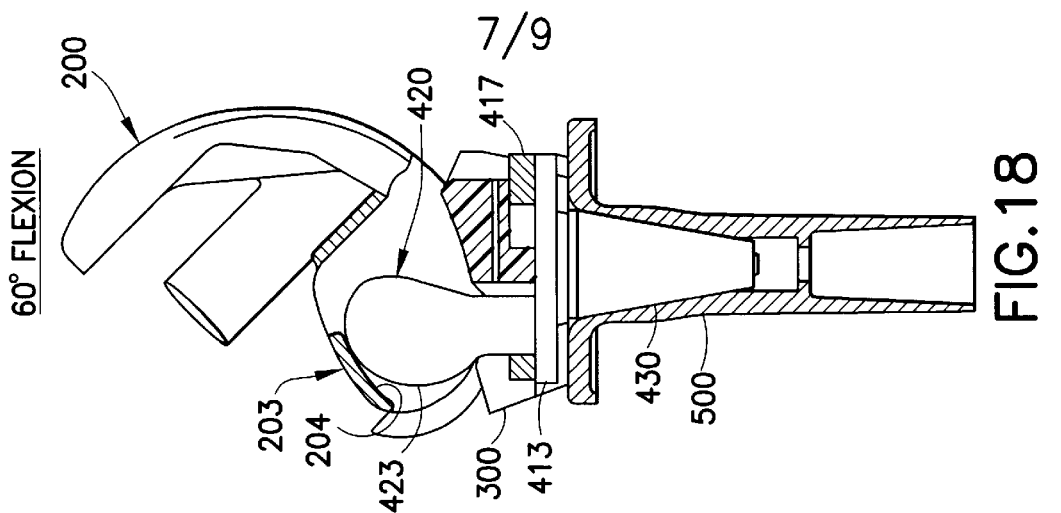
FIG. 18 is a cross-sectional view similar to FIGS. 16 and 17, but showing approximately 60° flexion.
Figure 17:
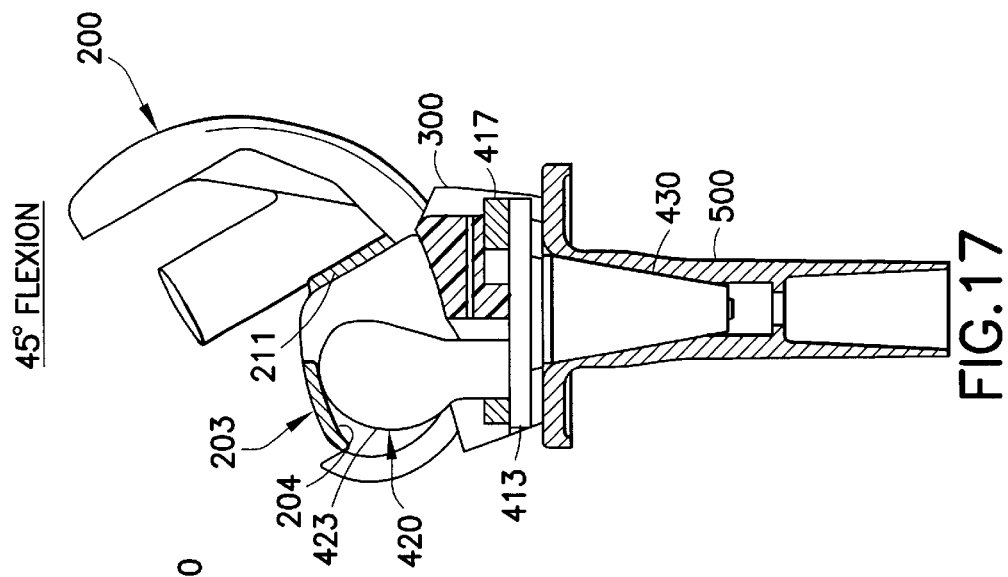
FIG. 17 is a cross-sectional view similar to FIG. 15, but showing approximately 45° flexion.

The control arm assembly 400, as shown in FIGS. 7–9, comprises a control arm 410, a post 420 and a conical bearing 430. The post 420 has medial and lateral side surfaces 421, an inferior recess 422, a post cam surface 423 and an anterior stop surface 424. The control arm 410 comprises a post support pin 412, a dovetail guide 413, a conical bearing support 414, a control arm boss 415 with control arm stop surfaces 416 and a stop pin 417.

The post 420 and conical bearing 403 preferably are formed from plastic and are assembled to the control arm 410 by pressing them on the post support pin 412 and conical bearing support 414 respectively. During assembly the inferior recess 422 of the post 420 engages the boss sidewalls 417 of the control arm 410 to prevent rotation of the post 420 on the post support pin 412. The tibial platform 500 has a superior bearing surface 501 and contains a conical hole 502 into which the conical bearing 403 of the control arm assembly 400 is placed on implantation. The tibial platform 500 can be the same as that described in U.S. Pat. No. 5,702,466. The embodiment shown here is a version used where an extension is added to the distal end of the platform to enhance fixation where needed.

The femoral component 200, the control arm 410 and tibial platform 500 preferably are made of titanium alloy coated with UltraCoat® TiN coating as disclosed in U.S. Pat. No. 5,702,448. However, these components can also be made of Co—Cr alloy. The bearing 300, post 420 and conical bearing 403 preferably are made of UHMWPe.

Figure 11:
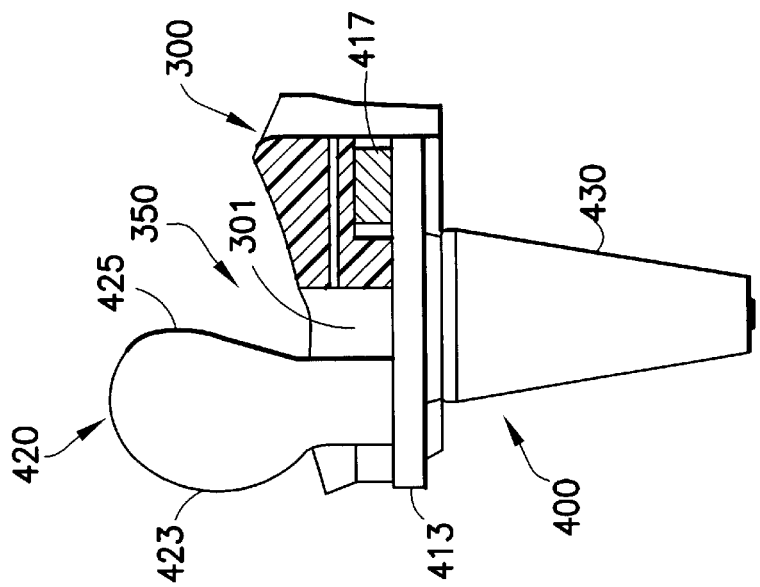
FIG. 11 is a side elevational view, partly in section, showing the subassembly of the bearing and control arm.
Figure 10:
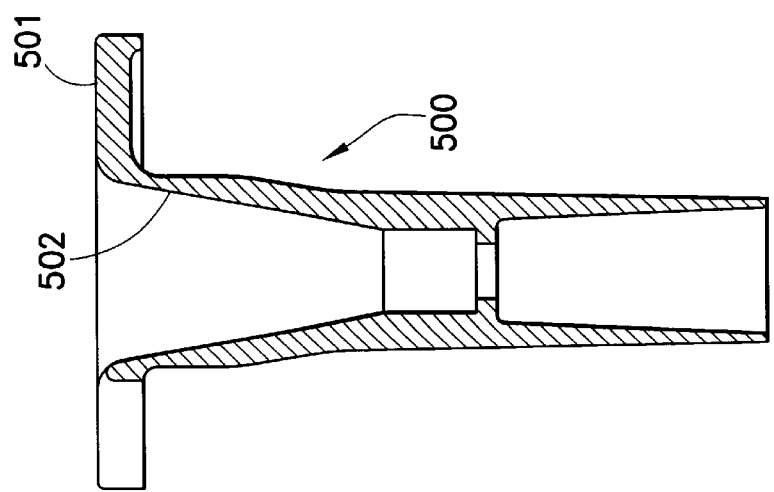
FIG. 10 is a cross-sectional view of the tibial component.

Implantation is illustrated in FIGS. 11–14. The tibial platform 500 is implanted into the tibia 600 and the femoral component assembly 900 consisting of the femoral component 200 with an attached extension 800 is inserted onto the femur 1000 in the usual fashion. The dovetail guide slot 302 of bearing 300 is engaged with the dovetail guide 413 of the control arm assembly 400 to produce a subassembly 350 as shown in FIG. 11. The subassembly 350 then is assembled onto the tibial platform 500 as shown in FIG. 12 and 13 with the knee 700 flexed to about 100°. The bearing 300 then is pressed digitally in a posterior direction until the bearing 300 is seated under the femoral component as shown in FIGS. 13 and 14.

There are two means of valgus-varus stability. Under load bearing conditions the normal compressive load will press the femoral condyles 206 against the matching articular bearing surfaces 310. The match is such that under compression any rotation of the femoral component 200, in the plane of FIG. 13 must occur around an axis 207 through the center of curvature 208 of the femoral condyle 206. Rotation about axis 207 produces impingement between the medial and lateral surfaces 421 and box sidewalls 202. This contact produces a reaction force that resists any valgus-varus moment applied to the joint. Thus, bending of the post 420 and post support pin 412 need not occur to resist the applied moment. The outer medial and lateral side surfaces 421 may be made to slope outward distal so as to increase contact area with cam box 201.

During non-load bearing phases where any valgus-varus moment is quite small, the post may be subject to small bending loads since joint compression may not occur. The post support pin 412 must be strong enough in bending to resist such moments.

The cooperative action of the cam box 201 and post cam surface 423 are illustrated in FIGS. 16–21. These figures show the outer posterior condyle 206 of the femoral component 200 broken away and the bearing in cross-section so as to show the action of the cam surfaces and the posterior bearing stop means. In full extension, as shown in FIG. 16, the cam box surface 204 and post cam surface 423 need not be in contact. At such flexion angles they do not act to prevent anterior-posterior dislocation in the absence of load bearing. Under load bearing the shape of the femoral articular surface 210 pressing against the tibial articular surface 310 provides stability and position.

As flexion progresses, as shown in FIGS. 17–21, the anterior wall 211 of the box cam 201 of the femoral component 200 moves away from the post 420 of the control arm assembly 400. This allows play or translation, as limited by various surfaces of the cam box 201 and post 420, the stop pin 417 and stop recess 303 or the stop surfaces 304 and 416. The femoral cam surface 204 will engage the post cam surface 423 at about 45°. At flexion below 45° the post cam surface 423 plays no role in providing roll back. Roll back up to about 7.5 mm nevertheless can occur at such low flexion with the subject invention. This roll back can be generated by the action of tension in the patella tendon, which tends to pull the tibia anteriorly. The 7.5 mm play allowed is relatively normal and certainly less than the play that is present in most current prosthetic knee designs. Translation motion of the bearing 300 is limited to about 7.5 mm and roll back after about 120° of flexion produces some acceptable amount of climb so as to limit excess posterior motion of the bearing 300, which might otherwise produce impingement with posterior structures of the knee, thereby inhibiting flexion.

FIGS. 17–21 show that at the full illustrated range of flexion angles, the contact between the femoral cam 203 and the post cam surface 423 is always concave-to-convex, thus allowing for moderate contact stress. This differs from convex-to-convex or convex-to-planar contact which would produce substantially higher contact stresses. FIG. 21 shows that the illustrated embodiment enables 155° of flexion. This value is significantly greater then needed for most Western peoples, and is sufficient for deflection preferred by Asian people where sitting style may require high degrees of flexion.

Fixed bearings prosthetic knees typically recess the patellar track. The recessing of the femoral patellar track is inconsistent with the use of a mobile patellar bearing and also has caused problems with fixed bearing designs. Climb, although a major problem with the conforming tibial bearing surfaces of the prior art low contact stress knee is not usually of great significance with the less conforming fixed bearing articulations. The embodiments disclosed here mobile bearing applications by making use of bearing mobility relative to the post and by avoiding disruption of the patellar track. More particularly, the prosthetic knee of this invention is novel in that it does not recess the patellar track. The knee also does not produce significant bending of the post from an applied valgus-varus moment during compressive load bearing. Additionally, the knee provides earlier initiation of rollback. Furthermore, the bearing moves with the femoral component during rollback thereby eliminating "climb" and thus maintaining best contact between the femoral and bearing articulating surfaces.

What is claimed is:

1. A knee joint prosthesis comprising:
   a femoral component having a superior surface for mounting to a femur, an inferior articular bearing surface with medial and lateral convex condyles, a cam box extending between the superior and inferior surfaces in a posterior portion of said femoral component, said cam box comprising medial and lateral walls;
   a tibial component;
   a bearing disposed between the femoral and tibial components, the bearing having a concave superior bearing face in articular bearing engagement with the convex condyles of the femoral component, the bearing further having an inferior bearing face in sliding and rotational bearing engagement with the tibial component, a notch extending anteriorly into a posterior face of the bearing and a groove formed in the inferior bearing face of the bearing and extending anteriorly from the notch; and
   a control arm assembly comprising a control arm slidably engaged in the groove of the bearing for permitting movement of the bearing along the control arm, pivotal connection means extending from the control arm for permitting pivotal movement of the control arm relative to the tibial component and a post extending superiorly from the control arm, the post being slidably engaged in the notch of the bearing and disposed in the cam box of the femoral component, the post having medial and lateral surfaces tapered away from one another at locations further from the control arm for increasing contact area with the medial and lateral walls of the cam box in response to valgus-varus moments.

2. The knee joint prosthesis of claim 1, wherein the concave superior bearing face of the bearing is configured for non-congruent bearing engagement with the convex condyles of the femoral component during selected ranges of flexion of the knee joint prosthesis.

3. The knee joint prosthesis of claim 1, wherein the cam box of the femoral component further comprises a cam wall extending between said medial and lateral walls and having a femoral cam surface, the post of the control arm assembly having a convex cam surface disposed for engaging the femoral cam surface and for generating roll back of the femoral component on the bearing during flexion of the knee joint.

4. The knee joint prosthesis of claim 3, wherein the femoral cam and the control arm are configured to engage one another after flexion of approximately 45°.

5. The knee joint prosthesis of claim 3, wherein the cam box further comprises an anterior wall extending between the medial and lateral walls.

6. The knee joint prosthesis of claim 5, wherein the post is configured for engaging the anterior wall when the knee joint prosthesis is in full extension.

7. The knee joint prosthesis of claim 3, wherein the cam surface of the post is a compound curve comprising a plurality of sequentially contiguous arc sections generated about parallel axes.

8. The knee joint prosthesis of claim 7, wherein the femoral cam surface defines a single concave curve generated about a medial-lateral axis.

9. The knee joint prosthesis of claim 3, wherein the femoral cam surface is aligned to face substantially in an inferior direction at full extension of said knee joint prosthesis.

10. The knee joint prosthesis of claim 1, wherein the control arm of the control arm assembly is formed from a metal material and wherein the post of the control arm assembly is formed from plastic.

11. The knee joint prosthesis of claim 10, wherein the control arm of the control arm assembly comprises a metallic post support pin, the plastic post being non-rotatably mounted on the metallic post support pin.

12. The knee joint prosthesis of claim 11, wherein the pivotal connection means of the control arm assembly comprises a conically generated bearing formed from a plastic material.

13. The knee joint prosthesis of claim 12, wherein the control arm of the control arm assembly includes a metallic conical bearing support, said conical bearing being mounted to the conical bearing support.

14. A knee joint prosthesis comprising:

a femoral component having a superior surface for mounting to a femur, an inferior articular bearing surface with medial and lateral convex condyles, a cam box extending between the superior and inferior surfaces in a posterior portion of said femoral component, said cam box comprising medial and lateral walls;

a tibial component;

a bearing disposed between the femoral and tibial components, the bearing having a concave superior bearing face in articular bearing engagement with the convex condyles of the femoral component, the bearing further having an inferior bearing face in sliding and rotational bearing engagement with the tibial component, a notch extending anteriorly into a posterior face of the bearing and a groove formed in the inferior bearing face of the bearing and extending anteriorly from the notch; and a control arm assembly comprising a control arm slidably engaged in the groove of the bearing for permitting movement of the bearing along the control arm, pivotal connection means extending from the control arm for permitting pivotal movement of the control arm relative to the tibial component and a post extending superiorly from the control arm, the post being slidably engaged in the notch of the bearing and disposed in the cam box of the femoral component, the post having medial and lateral surfaces tapered away from one another at locations further from the control arm for increasing contact area with the medial and lateral walls of the cam box in response to valgus-varus moments, the control arm including a stop pin projecting superiorly from an anterior portion of the control arm, the bearing including a stop recess in anterior portions of the dovetail guide slot, engagement of the stop pin with the stop recess preventing anterior dislocation of said bearing relative to said control arm and said tibial component.

15. The knee joint prosthesis of claim 14, wherein the stop pin is formed from a metallic material.

* * * * *